US00PP13719P29

(12) United States Plant Patent
Danziger

(10) Patent No.: US PP13,719 P2
(45) Date of Patent: Apr. 8, 2003

(54) ARGYRANTHEMUM PLANT NAMED 'DANARNEP'

(75) Inventor: Gabriel Danziger, Nir-Zvi (IL)

(73) Assignee: Danziger - "Dan" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 10/120,426

(22) Filed: Apr. 12, 2002

(51) Int. Cl.[7] ..... A61M 5/00

(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—Foley & Lardner

(57) ABSTRACT

A new and distinct Argyranthemum plant named 'Danarnep' characterized by having white oblong ray florets and yellow bell-shaped disc florets; bush type vigorous growth; use in the garden as a single plant or planted in groups as well as use as a border plant and suitable for planting in pots; and growth in full sunlight or partial shade.

1 Drawing Sheet

LATIN NAME OF THE GENUS AND SPECIES OF THE PLANT CLAIMED

*Argyranthemum frutescens.*

VARIETY DENOMINATION

'Danarnep'; commercially, Argyranthemum cv. Neptune.

BACKGROUND OF THE INVENTION

The present invention relates to a new and distinct cultivar of Argyranthemum plant, botanically known as *Argyranthemum frutescens*, hereinafter referred to by the cultivar name 'Danarnep'.

The new cultivar originated from a cross made in a controlled breeding program in Moshav Mishmar Hashiva, Israel. The female parent is 'AV02', an unpatented propriety cultivar of the inventor's. The male parent is 'AV008', an unpatented propriety cultivar of the inventor's. 'Danarnep' was discovered and selected by the inventor, Gabriel Danziger, as a flowering plant within the progeny of the stated cross in a controlled environment in Moshav Mishmar Hashiva, Israel.

Asexual reproduction of the new cultivar by stem cutting was first performed in April, 1998 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danarnep' which in combination distinguish this Argyranthemum as a new and distinct cultivar:

1. White oblong ray florets and yellow bell-shaped disc florets;

2. Bush type vigorous growth;

3. Early flowering;

4. Use in the garden as a single plant or planted in groups as well as use as a border plant and suitable for planting in pots; and 5. Growth in full sunlight or partial shade.

'Danarnep' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Danarnep' is cultivar 'Dana' (unpatented).

| Characteristic | 'Danarnep' | 'Dana' |
|---|---|---|
| Flower Size | 40–43 mm | 32–35 mm |
| Flowering Time | Early | Medium |
| Growth Potency | High | Medium |
| Growth Habit | Compact | Compact |

BRIEF DESCRIPTION OF THE DRAWING

The accompanying photographic drawing illustrates the overall appearance of the new Argyranthemum showing the colors as true as is reasonably possible with colored reproductions of this type. The photograph shows a flowering 'Danarnep' in its entirety.

DETAILED BOTANICAL DESCRIPTION

The following observations, measurements and values describe the new cultivar as grown in Moshav Mishmar Hashiva, Israel under conditions which closely approximate those generally used in commercial practice. Outdoor in private gardening or landscape as bedding plant. Irrigate and fertilize on regular bases using moderate regin. Color references are made to The Royal Horticultural Society Colour Chart (R.H.S.), except where general colors of ordinary significance are used. Color values were taken under daylight conditions at approximately 12:00 p.m. in Moshav Mishmar Hashiva, Israel. The age of the plant described is 14 weeks from planting.

Propagation: Stem cutting.

PLANT

General appearance and form:

*Height.*—30–35 cm.

*Width.*—30–35 cm.

*Branching.*—Densely branched.

*Flowering response.*—Short day response. Flowering Season: During winter and spring until summer. Winter Hardiness: Hardy in moderate climate. Lastingness of the Individual Bloom: 15–17 days. Rooting Habit: Adventitious roots from cutting base. Time to initiate roots: 10–12 days. Time to produce a rooted cutting or liner: 18–20 days. Growth and branching habit: Bush type densely branched. Crop time: 12–14 weeks for a 10 cm flowering pot ready for sale. Fragrance: None.

Foliage:

*Overall shape of leaf.*—Pinnatipartite.

*Apex.*—Rounded.

*Base.*—Wedge-shaped.

*Length.*—65–70 mm.

*Width.*—40–45 mm.

*Margin.*—Serrate.

*Texture.*—Slightly warty.

*Durability to stresses.*—Maintains growth and flowering during moderate winter.

*Color of upper surface.*—Mature leaf: Green group 137-A. Immature leaf: Green group 137-B.

*Color of lower surface.*—Mature leaf: Green group 137-C. Immature leaf: Green group 137-D.

*Venation color.*—Upper surface: Green group 137-B. Lower surface: Green group 137-C.

*Petiole.*—Length: 12–15 mm. Diameter: 2–3 mm. Color: Green group 137-C.

Inflorescence:

*Flowering response.*—Short day response.

*Inflorescence bud.*—Height: 4–5 mm. Diameter: 5–6 mm. Color: Gray-Brown group 199-B.

*Inflorescence size.*—Diameter: 40–43 mm. Depth (height): 4–5 mm. Diameter of disc: 5–6 mm.

*Ray florets.*—Shape: Oblong. Length: 15–17 mm. Width: 4–5 mm. Apex: 3–4 mm, rounded. Margin: Entire. Texture: Smooth. Number of ray florets per inflorescence: 17–20. Color when opening: White 155-D. Color when fully opened upper surface: White 155-D. Color when fully opened lower surface: White 155-C.

*Disc florets.*—Shape: Bell-Shaped (campanula). Length: 3–4 mm. Width: 1 mm. Apex: Toothed. Margin: Entire. Texture: Smooth. Number of disc florets per inflorescence: 180–200. Color when opening: Color when fully opened upper surface: Yellow group 9-A. Color when fully opened lower surface: Yellow group 9-C.

*Stem.*—Average length: 30–35 cm. Average diameter: 6–8 mm. Color: Yellow-Green 144-A. Internode length: 25–30 mm. Phyllaries (Sepals): Quantity and arrangement: 15 attached to the receptacle bottom. Aspect: Oval. Apex: Rounded (Obtuse). Margin: Entire. Length: 2–3 mm. Upper surface color: Yellow-Green 144-C. Lower surface color: Yellow-Green 144-B.

*Peduncles.*—Length: 6–7 cm. Diameter: 1.5–2 mm. Texture: Slightly Warty. Color: Yellow-Green 146-B.

Reproductive organs:

*Stamen.*—Number: 5 fused as tube. Color: Yellow 13A.

*Seeds.*—Width: 1 mm. Length: 2 mm. Shape: Achene. Color: Grayed-Yellow 161-A.

*Fruit.*—Achene. Color: Grayed-Yellow 161-A.

*Anthers.*—Color: Yellow 13-A.

*Pollen.*—Color: Yellow 13-A.

*Stigma.*—Color: Yellow 12-B.

*Ovary.*—Color: Yellow-Green 149-D.

Disease resistance: Unknown, no susceptibility was observed under regular growing conditions.

I claim:

1. A new and distinct Argyranthemum plant named 'Danarnep', substantially as illustrated and described herein.

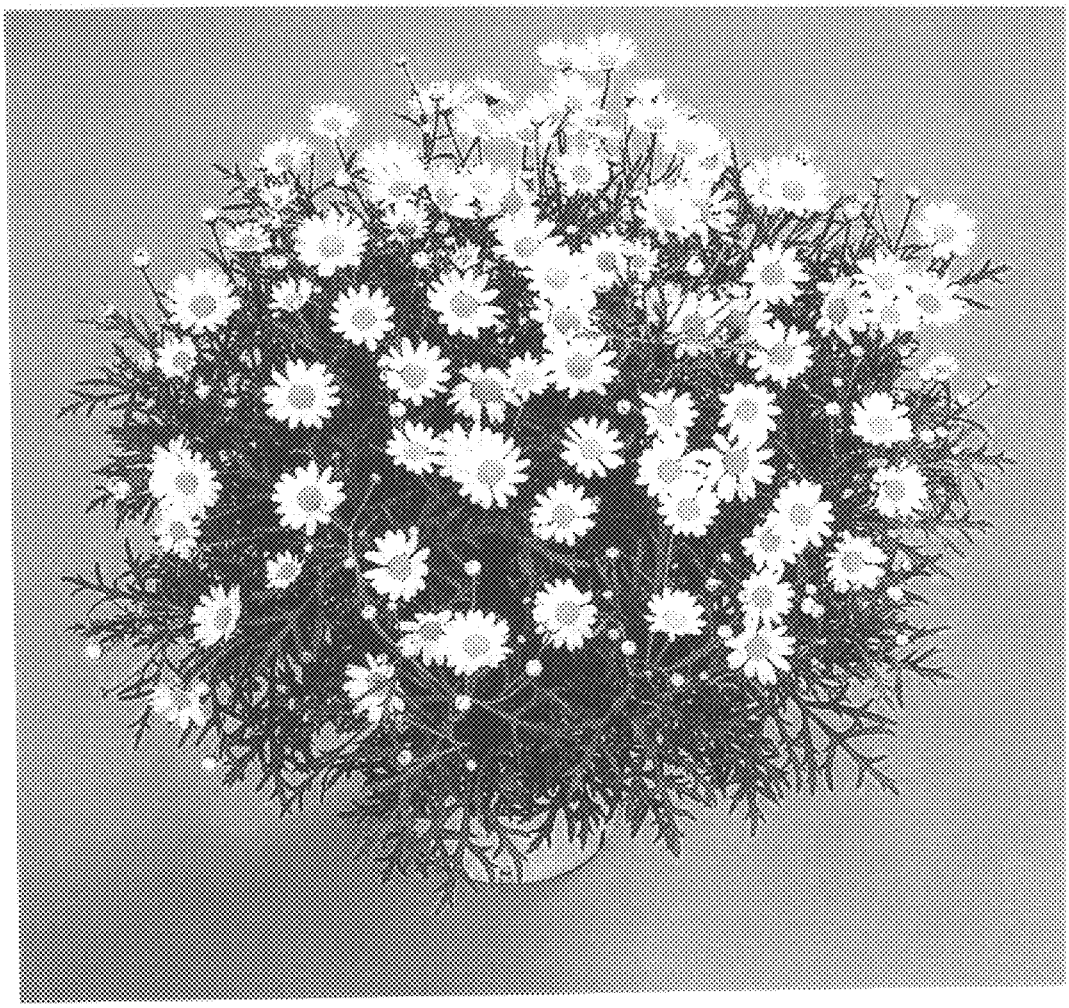

* * * * *